United States Patent
Agarkhed et al.

(10) Patent No.: US 11,224,562 B2
(45) Date of Patent: Jan. 18, 2022

(54) TOPICAL ANTIMICROBIAL COMPOSITION

(71) Applicant: Conopco, Inc., Englewood Cliffs, NJ (US)

(72) Inventors: Ajit Manohar Agarkhed, Thane (IN); Mohini Anand Bapat, Mumbai (IN); Amitabha Majumdar, Bangalore (IN); Prathyusha Mallemala, Bangalore (IN); Mruthyunjaya Swamy Mathapathi, Bangalore (IN); Nikita Tomar, Nagpur (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/098,940

(22) PCT Filed: Apr. 11, 2017

(86) PCT No.: PCT/EP2017/058620
§ 371 (c)(1),
(2) Date: Nov. 5, 2018

(87) PCT Pub. No.: WO2017/194256
PCT Pub. Date: Nov. 16, 2017

(65) Prior Publication Data
US 2019/0175473 A1    Jun. 13, 2019

(30) Foreign Application Priority Data

May 10, 2016 (EP) ..................... 16168875

(51) Int. Cl.
| | |
|---|---|
| *A61K 8/41* | (2006.01) |
| *A61K 8/67* | (2006.01) |
| *A61Q 17/00* | (2006.01) |
| *A61Q 19/10* | (2006.01) |
| *A61K 31/455* | (2006.01) |
| *A61K 31/14* | (2006.01) |
| *A61K 9/00* | (2006.01) |
| *A61P 31/02* | (2006.01) |
| *A61K 45/06* | (2006.01) |
| *A61K 9/08* | (2006.01) |

(52) U.S. Cl.
CPC .............. *A61K 8/416* (2013.01); *A61K 8/675* (2013.01); *A61K 9/0014* (2013.01); *A61K 31/14* (2013.01); *A61K 31/455* (2013.01); *A61K 45/06* (2013.01); *A61P 31/02* (2018.01); *A61Q 17/005* (2013.01); *A61Q 19/10* (2013.01); *A61K 9/08* (2013.01); *A61K 2300/00* (2013.01); *A61K 2800/5922* (2013.01)

(58) Field of Classification Search
CPC .......... A61K 8/416; A61K 8/675; A61P 31/02
See application file for complete search history.

(56) References Cited

U.S. PATENT DOCUMENTS

| | | | |
|---|---|---|---|
| 2010/0222433 A1 | 9/2010 | Xue et al. | |
| 2013/0035396 A1* | 2/2013 | Moen ..................... | A01N 33/12 |
| | | | 514/643 |
| 2015/0050342 A1* | 2/2015 | Lowe ................... | A61K 36/815 |
| | | | 424/489 |

FOREIGN PATENT DOCUMENTS

| | | |
|---|---|---|
| CN | 101583572 | 11/2009 |
| CN | 104244715 | 12/2014 |
| WO | WO03061610 | 7/2003 |
| WO | WO2013014427 | 1/2013 |
| WO | WO2013017967 | 2/2013 |
| WO | WO2013116053 | 8/2013 |

OTHER PUBLICATIONS

Hautklinik et al.; Nicotini acid/niacinamide and the skin; Journal of Cosmetic Dermatology; Jan. 1, 2004; p. 88-93 accepted for publication Aug. 19, 2004; vol. 3 No 2; United States of America.
Search Report and Written Opinion in PCTEP2017058620; dated Jul. 14, 2017.
Search Report & Written Opinion in EP16168875; dated Sep. 27, 2016.
Gehring W.; Nicotinic acid/niacinamide and the skin; Journal of Cosmetic Dermatology; Jan. 1, 2004; pp. 88-93, XP008080589; vol. 3 No 2; Blackwell Science; United Kingdom.
IPRP1 in PCTEP2017058620; dated Nov. 13, 2018.

* cited by examiner

*Primary Examiner* — Michael B. Pallay
(74) *Attorney, Agent, or Firm* — Krista A. Kostiew

(57) ABSTRACT

The present invention relates to a topical composition. The present invention more particularly relates to a topical composition for antimicrobial benefit and a method of disinfecting a surface. According to the invention there is provided a topical composition comprising: a) 0.1 to 10% by weight of Niacinamide or its derivatives; b) 0.01% to 5% by weight of a first quaternary ammonium salt comprising Didecyl Dimethyl Ammonium Chloride; c) 0.01 to 5% by weight of a second quaternary ammonium salt; and d) a cosmetically acceptable base.

11 Claims, No Drawings

TOPICAL ANTIMICROBIAL COMPOSITION

CROSS REFERENCE TO RELATED APPLICATIONS

The present application is a U.S. National Phase Application under 35 U.S.C. § 371 of International Application No. PCT/EP2017/058620 filed on Apr. 11, 2017, which claims priority to European patent application No. 16168875.9 filed on May 10, 2016, the contents of which are incorporated herein in their entireties.

TECHNICAL FIELD

The present invention relates to a topical composition. The present invention more particularly relates to a topical composition for antimicrobial benefit and a method of disinfecting a surface.

BACKGROUND OF THE INVENTION

People try to take good care of the external surface of their bodies as well as those of their pets to enable good overall health. Specific skin related issues that people care about include, good skin health free of infections, good skin tone and skin hygiene. Skin hygiene is generally achieved by keeping them free of infections. One way to tackle infections is to treat them with antimicrobials after the infection has set in. Another approach is to leave a minimal amount of antimicrobial active on the surface so that any invading microorganism is killed or inactivated so as to minimize spread of disease. Yet another approach is improving the innate immunity of the desired surface.

WO 13/017967 (KIMBERLY CLARK, 2013) discloses an antimicrobial cleansing composition comprising: a polar carrier solvent; from about 0.1 percent (w/w) to about 15 percent (w/w) cationic compatible surfactant; from about 0.01 percent (w/w) to about 10 percent (w/w) quaternary ammonium biocide; and a cationic compatible after feel agent, wherein the antimicrobial cleansing composition is substantially free of a betaine-based surfactant and substantially free of a compound selected from the group consisting of triclosan, triclocarban, a halogenated phenolic antimicrobial agent, and combinations thereof.

WO 03/061610 (WALKER, 2003) discloses Germicidal compositions with enhanced activity towards killing microbiolical spores and vetgetative cells comprising certain quaternary ammonium compounds (QACs), phenolic compounds, monohydric alcohols, hydrogen peroxide, iodeine, triclocarban, triclosan or combinations thereof with one or more spore coat opening agents. The invention also provides for the application of the germicidal compositions to animate and inanimate surfaces to help kill germs and protect against the risk of infection from bacteria, molds, yeasts, fungi, viruses, and microbiological spores.

US 2010 222433 (SHANGHAI JIUYU BIOLOGICAL TECHNOLOGY, 2010) Discloses A composite disinfectant cleaner which, on a total composition weight basis, comprises: (a) about 0.5-0.7 weight percent of an alkyl dimethyl benzyl ammonium chloride (b) about 0.3-0.5 weight percent of an octyl decyl dimethyl ammonium chloride (c) about 0.1-0.2 weight percent of a dioctyl dimethyl ammonium chloride (d) about 0.2-0.3 weight percent of a didecyl dimethyl ammonium chloride (e) about 0.5-2 weight percent of an alkylamine (f) about 0.3-1.5 weight percent of a guanidine (g) about 10-20 weight percent of a penetrant (h) about 5-10 weight percent of a surfactant (i) about 0.1-0.6 weight percent of a chelant (j) about 0.05-0.1 weight percent of an essence (k) the balance being deionized water.

Specifically in the present days the number of contagious diseases are spreading more rapidly as we are exposed to social life like never before. We greet people by shaking hands and then we use the same hands for eating foods. Therefore there is always a chance of spreading contagious disease causing microbes from one person to another either though hand or any other kinds of contact. The currently available alcohol based sanitizers are able to kill the microbes just after the contact. However these sanitizers are unable to protect the hands for longer period of time to create an innate immunity as desired.

It is thus an object of the present invention to provide a topical composition.

It is another object of the present invention to provide an antimicrobial composition.

It is a further object of the present invention to provide a topical composition that provides innate immunity to a topical surface of a human or animal body.

It is yet another object of the present invention to provide a hand sanitizer composition.

It is yet a further object of the present invention to provide a topical composition which provides long lasting antimicrobial benefits.

The present inventors while extensively working on this problem have surprisingly found out that a topical composition comprising Niacinamide or its derivatives, a first quaternary ammonium salt comprising Dodecyl Dimethyl Ammonium Chloride and a second quaternary ammonium salt when combined together in a particular ratio able to provide an antimicrobial composition which provides long lasting antimicrobial benefit and thereby satisfying one or more of the objects of the invention.

SUMMARY OF THE INVENTION

In a first aspect of the present invention there is provided an antimicrobial composition comprising:
  a) 0.1 to 10% by weight of Niacinamide or its derivatives;
  b) 0.01% to 5% by weight of a first quaternary ammonium salt comprising Didecyl Dimethyl Ammonium Chloride;
  c) 0.01 to 5% by weight of a second quaternary ammonium salt; and
  d) a cosmetically acceptable base.

In a second aspect of the present invention there is provided a method of disinfecting a surface comprising the steps of applying a composition of the first aspect on to said surface.

Any feature of one aspect of the present invention may be utilized in any other aspect of the invention. The word "comprising" is intended to mean "including" but not necessarily "consisting of" or "composed of." In other words, the listed steps or options need not be exhaustive. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

The present invention provides a topical composition comprising:
 a) 0.1 to 10% by weight of Niacinamide or its derivatives;
 b) 0.01% to 5% by weight of a first quaternary ammonium salt comprising Didecyl Dimethyl Ammonium Chloride;
 c) 0.01 to 5% by weight of a second quaternary ammonium salt; and
 d) a cosmetically acceptable base.

One of the component of the composition of the present invention is Niacinamide or its derivatives. Niacinamide is also known as Nicotinamide or Nicotinic acid amide or vitamin B3. It is a water soluble vitamin having the following structure:

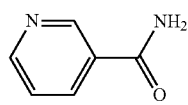

Niacinamide has anti-inflammatory actions. This is also known for treating acne. For the purpose of the present invention Niacinamide or its derivatives is an essential component of the composition. The derivatives of Niacinamide may be any derivatives. Any isomer or derivatives of niacinamide that are having similar property to niacinamide may preferably be used.

The preferred structure of derivative of Niacinamide is as follows:

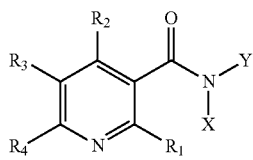

Wherein $R_1$, $R_2$, $R_3$, $R_4$, X, Y may preferably be any group selected from H, $C_1$ to $C_{18}$ saturated or unsaturated, liner or branched or cyclic hydrocarbon.

Any precursors of niacinamide that are having similar property to niacinamide are also within the scope of the present invention.

The amount of Niacinamide is in the range of 0.1 to 10%, preferably 0.5 to 8%, more preferably 1 to 6% and most preferably 2 to 5% by weight of the composition.

The composition of the present invention also comprises 0.01% to 5% by weight of a first quaternary ammonium salt comprising Didecyl Dimethyl Ammonium Chloride. Most preferably, the first quaternary ammonium salt is Didecyl Dimethyl Ammonium Chloride or DDAC.

The present inventors have surprisingly found that a quaternary ammonium salt comprising DDAC when combined with any other quaternary ammonium salt most preferably quaternary ammonium biocide it is able to provide synergistic combination with niacinamide or its derivatives.

Didecyl Dimethyl Ammonium Chloride (DDAC) is a known disinfectant used in many biocidal formulations. It has the following structure:

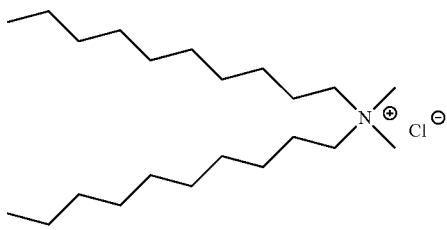 [SMILES: CCCCCCCCCC[N+](C)(C)CCCCCCCCCC ; [Cl-]]

The amount of the first quaternary ammonium salt comprising DDAC preferably is in the range of 0.01 to 2%, preferably 0.05 to 1% and most preferably 0.05 to 0.5% by weight of the composition.

The present invention also comprises 0.01 to 5% by weight of a second quaternary ammonium salt. The most preferred quaternary ammonium salt being quaternary ammonium biocide.

The second quaternary ammonium salt may preferably be selected from Benzethonium Chloride (BEC), Benzalkonium chloride (BKC) or Polydiallyldimethylammonium chloride (polyDADMAC).

Benzethonium chloride (BEC) also known as hyamine which is a quaternary ammonium salt. It is known for its disinfectant properties and having the following structure:

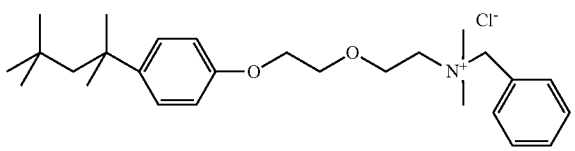 [SMILES: CC(C)(C)CC(C)(C)c1ccc(OCCOCC[N+](C)(C)Cc2ccccc2)cc1 ; [Cl-]]

BEC is known for its antiseptic and anti-infective properties. It has been known to be used in cosmetic and toiletries compositions.

The amount of BEC is in the range of 0.01 to 1%, preferably 0.05 to 1% and most preferably 5 0.05 to 0.5% by weight of the composition.

Benzalkonium chloride (BKC) also known as alkyldimethylbenzylammonium chloride. It is known to be used as a cationic surfactant and as a biocide. It has the following structure:

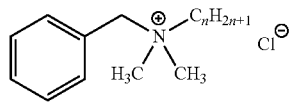

n = 8, 10, 12, 14, 16, 18

The amount of BKC is in the range of 0.01 to 1%, preferably 0.05 to 1% and most preferably 0.05 to 0.5% by weight of the composition.

Polydiallyldimethylammonium chloride is also known as polyDADMAC. It is a homo-polymer of diallyldimethylammonium chloride. The charge density for polyDADMAC is high, hence it is generally used in flocculation. It has the following structure:

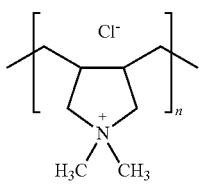

The amount of polyDADMAC is in the range of 0.01 to 1%, preferably 0.05 to 1% and most preferably 0.05 to 0.5% by weight of the composition.

The composition of the present invention preferably in the form of a leave-on composition. The leave-on composition may be in the form of vanishing cream or may be in the form of a sanitizer composition. The most preferred application being the hand sanitization.

The cosmetically acceptable base is preferably a cream, lotion, gel or emulsion. Personal care compositions (leave-on) may be prepared using different cosmetically acceptable emulsifying or non-emulsifying systems and vehicles. A highly suitable base is a cream. Vanishing creams are especially preferred. Vanishing cream bases generally comprise 5 to 25% fatty acid and 0.1 to 10% soap. Vanishing cream base gives a highly appreciated matty feel to the skin. C12 to C20 fatty acids are especially preferred in vanishing cream bases, further more preferred being C14 to C18 fatty acids. The most preferred fatty acid is stearic acid. The fatty acid in the composition is more preferably present in an amount in the range of 5 to 20% by weight of the composition. Soaps in the vanishing cream base include alkali metal salt of fatty acids, like sodium or potassium salts, most preferred being potassium stearate. The soap in the vanishing cream base is generally present in an amount in the range of 0.1 to 10%, more preferably 0.1 to 3% by weight of the composition. Generally, the vanishing cream base in personal care compositions is prepared by taking a desired amount of total fatty matter and mixing with potassium hydroxide in desired amounts. The soap is usually formed insitu during the mixing.

An especially suitable cosmetically acceptable base is one which comprises a water-in-oil emulsion comprising silicone oils as the continuous phase. The water in oil emulsions preferably comprise a cross-linked silicone elastomer blend.

Inclusion of silicone elastomer blend in a water-in-oil emulsion may be used as the cosmetically acceptable base for preparing the compositions of the present invention. While silicone fluids may be used, silicone elastomers which are cross-linked, are especially preferred. The creation of cross-linkages between linear polymers, such as dimethicone, converts the linear polymer into a silicone elastomer. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions.

Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer]; EL-8050 [INCI Name: Isododecane (and) Dimethicone/Bis-Isobutyl PPG 20 Crosspolymer] DC9040, DC9041, DC9045 (Dimethicone crosspolymer); DC 9506, 9509 (Dimethicone vinyl dimethicone crosspolymer); Shin-Etsu KSG-15, KSG-16, KSG-17 (Dimethicone vinyl dimethicone crosspolymer). It is further preferred that the composition comprises 5 to 50% silicone elastomer by weight of the composition.

In the case of wash-off composition, In addition to the essential ingredients as described earlier, preferred embodiments of the cleansing compositions may also include other optional and preferred ingredients for their known benefits. The type and content will largely depend on the nature and type of cleansing composition as well as general principles of formulation science.

Where the composition is in the form of a bar of soap or a liquid soap, it is preferred that the composition contains free fatty acids. Preferred embodiments contain 0.01 wt % to 10 wt % free fatty acid, especially when major portion of the surfactant is soap based. Potentially suitable fatty acids are C8 to C22 fatty acids. Preferred fatty acids are C12 to C18, preferably predominantly saturated, straight-chain fatty acids. However, some unsaturated fatty acids can also be employed. Of course the free fatty acids can be mixtures of shorter chain length (e.g., C10 to C14) and longer chain-length (e.g., C16-C18) chain fatty acids. For example, one useful fatty acid is fatty acid derived from high-laurics triglycerides such as coconut oil, palm kernel oil, and babasu oil. The fatty acid can be incorporated directly or they can be generated in-situ by the addition of a protic acid to the soap during processing. Examples of suitable protic acids include: mineral acids such as hydrochloric acid and sulfuric acid, adipic acid, citric acid, glycolic acid, acetic acid, formic acid, fumaric acid, lactic acid, malic acid, maleic acid, succinic acid, tartaric acid and polyacrylic acid. However, care should be taken that the residual electrolyte in the bar does not substantially reduce the effectiveness of the anticracking agent. The level of fatty acid having a chain length of 14 carbon atoms and below should generally not exceed 5.0%, preferably not exceed about 1% and most preferably be 0.8% or less based on the total weight of the continuous phase.

Water soluble/dispersible polymers is an optional ingredient that is highly preferred to be included in composition. These polymers can be cationic, anionic, amphoteric or nonionic types with molecular weights higher than 100,000 Dalton. They are known to increase the viscosity and stability of liquid cleanser compositions, to enhance in-use and after-use skin sensory feels, and to enhance lather creaminess and lather stability. Amount of the polymers, when present, may range from 0.1 to 10% by weight of the composition.

Examples of water soluble/or dispersible polymers include the carbohydrate gums such as cellulose gum, microcrystalline cellulose, cellulose gel, hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, xanthan gum and mixtures thereof; modified and nonmodified starch granules and pregelatinized cold water soluble starch; emulsion polymers such as Aculyn® 28, Aculyn® 22 or Carbopol® Aqua SF1; cationic polymer such as modified polysaccharides including cationic guar available from Rhone Poulenc under the trade name Jaguar® C13S, Jaguar® C14S, Jaguar® C17, or Jaguar® C16; cationic modified cellulose such as UCARE® Polymer JR 30 or JR 40 from Amerchol; N-Hance® 3000, N-Hance® 3196, N-Hance® GPX 215 or N-Hance® GPX 196 from Hercules;

synthetic cationic polymer such as Merquat® 100, Merquat® 280, Merquat® 281 and Merquat® 550 sold by Nalco; cationic starches such as StaLok® 100, 200, 300 and 400 sold by Staley Inc.; cationic galactomannans such as Galactasol® 800 series by Henkel, Inc.; Quadrosoft® LM-200; and Polyquaternium-24®. Also suitable are high molecular weight polyethylene glycols such as Polyox® WSR-205 (PEG 14M), Polyox® WSR-N-60K (PEG 45), and Polyox® WSR-301 (PEG 90M).

The composition of the invention may additionally comprise a skin-lightening agent. Apart from niacinamide which is anyway presence as one of the essential component of the present composition, other well known skin lightening agents e.g. aloe extract, ammonium lactate, arbutin, azelaic acid, kojic acid, butyl hydroxy anisole, butyl hydroxy toluene, citrate esters, 3 diphenyl propane derivatives, 2, 5 dihydroxybenzoic acid and its derivatives, ellagic acid, fennel extract, gluco pyranosyl-1-ascorbate, gluconic acid, glycolic acid, green tea extract, hydroquinone, 4 hydroxyanisole and its derivatives, 4-hydroxy benzoic acid derivatives, hydroxycaprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof.

Preferably, the composition may have sunscreen. Any sunscreen that can be suitably used with the base may be added. Both, UVA and UVB sunscreens may preferably be added.

The composition of the invention preferably comprises a UV-A sunscreen which is a dibenzoylmethane or its derivatives. Preferred dibenzoylmethane derivatives are selected from 4-tert-butyl-4'-methoxydibenzoylmethane, 2-methyl-dibenzoylmethane, 4-methyl-dibenzoylmethane, 4-isopropyldibenzoyl-methane, 4-tert-butyldibenzoylmethane, 2,4-dimethyldibenzoylmethane, 2,5-dimethyldibenzoyl-methane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane. The most preferred dibenzoylmethane derivative is 4-tert.-butyl-4'-methoxydibenzoylmethane. The composition of the invention preferably comprises 0.1 to 10%, more preferably 0.2 to 5%, further more preferably 0.4 to 3%, by weight dibenzoylmethane or a derivative thereof based on total weight of the composition and including all ranges subsumed therein.

The composition preferably comprises a UV-B organic sunscreen selected from the class of cinnamic acid, salicylic acid, diphenyl acrylic acid and derivatives thereof. Illustrative non-limiting example of UV-B sunscreens which are commercially available and useful for inclusion in the composition of the invention are Octisalate™, Homosalate™, NeoHelipan™, Octocrylene™, Oxybenzone™ or Parsol MCX™. The UV-B sunscreen is most preferably 2-ethyl-hexyl-4-methoxy cinnamate which is commercially available as Parsol MCX. The UV-B organic sunscreen is preferably included in 0.1 to 10%, more preferably 0.1 to 7% by weight of the composition. It has been observed that presence of an organic UV-B sunscreen like 2-ethyl-hexyl-4-methoxy cinnamate causes further rapid degradation of the UV-A dibenzoylmethane sunscreen in the presence of UV radiation. The presence of the rosmarinic acid ester compound is found to be very efficacious in stabilizing the composition even when UV-B sunscreens are present.

Useful inorganic sun-blocks are also preferably used in the present invention. These include, for example, zinc oxide, iron oxide, silica, such as fumed silica, and titanium dioxide.

Preservatives can also be added into the compositions to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibility between the preservatives and other ingredients. Preservatives are preferably employed in amounts ranging from 0.01% to 2% by weight of the composition.

A variety of other optional materials may be formulated into the compositions. These may include: antimicrobials such as 2-hydroxy-4,2',4'-trichlorodiphenylether (triclosan), 2,6-dimethyl-4-hydroxychlorobenzene, and 3,4,4'-trichlorocarbanilide; scrub and exfoliating particles such as polyethylene and silica or alumina; cooling agents such as menthol; skin calming agents such as aloe vera; and colorants.

In addition, the compositions may further include 0 to 10% by weight of opacifiers and pearlizers such as ethylene glycol distearate, titanium dioxide or Lytron® 621 (Styrene/Acrylate copolymer); all of which are useful in enhancing the appearance or properties of the product.

Diluents other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Solvents, such as ethyl alcohol, isopropanol, acetone, ethylene glycol monoethyl ether, diethylene glycol monobutyl ether, diethylene glycol monoethyl ether;

In case of soap bars, it may contain particles that are greater than 50 μm in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves;

microcrystalline wax beads; jojoba ester beads, and the like. These exfoliants come in a variety of particle sizes and morphology ranging from micron sized to a few mm. They also have a range of hardness. Some examples are talc, calcite, pumice, walnut shells, dolomite and polyethylene.

Advantageously, active agents other than skin conditioning agents defined above may be added to the composition. These active ingredients may be advantageously selected from bactericides, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; or mixtures thereof; and the like.

These active agents may be selected from water-soluble active agents, oil soluble active agents, pharmaceutically acceptable salts and mixtures thereof. The term "active agent" as used herein, means personal care actives which can be used to deliver a benefit to the skin and/or hair and which generally are not used to confer a skin conditioning benefit, such as are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent(s) will vary with the specific active agent, the ability of the active to penetrate through the skin, the age, health condition, and skin condition of the user, and other like factors.

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable base is usually from 10 to 99.9%, preferably from 50 to 99% by weight of the composition, and can, in the absence of other personal care adjuncts, form the balance of the composition.

The composition of the invention may comprise a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition. Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% by weight of the composition and in many instances from 40 to 80%. Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C. Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice is most often ethanol or sometimes iso-propanol. Polyhydric alcohols commonly comprise ethylene or propylene glycol, or a homologue can be employed such as diethylene glycol. Other than this suitable other vehicle and component used for deodorant composition can be added.

Preferably, when the composition is in the form of a hand sanitizer composition the cosmetically acceptable base may comprises of alcohol and water. The most preferred alcohols are ethyl alcohol and isopropyl alcohol. Even a mixture of two or more alcohol can preferably be used in the hand sanitizer composition. The amount of alcohol preferably in the range of 50 to 95%, more preferably 60 to 80% and most preferably 65 to 80% by weight of the hand sanitizer composition.

The compositions of the present invention can comprise a wide range of other optional components. The CTFA Personal care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, pH adjusters, natural extracts, essential oils, skin sensates, skin soothing agents, and skin healing agents.

The present invention also discloses a method of cleaning or disinfecting a surface comprising the steps of applying a composition according to the invention on to said surface in case of a leave-on composition. This method comprises an additional step of at least partially removing the composition wherein the composition is in the form of a wash-off composition. Preferably, the step of at least partially removing the composition is carried out less than 5 minutes after the step of applying the composition on the substrate. The surface is preferably human skin or any other hard surfaces. The most preferred surface is human skin. The preferred method of cleaning or disinfecting a surface of the present invention is non-therapeutic and/or cosmetic.

The present invention also discloses a use of a composition of the present invention as disclosed above for improved antimicrobial benefit. More particularly the present invention discloses the use of Niacinamide or its derivatives, a first quaternary ammonium salt comprising Didecyl Dimethyl Ammonium Chloride and a second quaternary ammonium salt in a topical composition for synergistic antimicrobial benefit.

Synergistic antimicrobial benefit preferably means the composition of the invention able to provide significantly better antimicrobial benefit when the individual component of the present composition used alone. We have found that, after application of the composition of the present invention the residual microbes on the surface is significantly less. Therefore the composition of the present invention able to provide prolonged/long-lasting antimicrobial benefits. The preferred intended use of the composition of the present invention is non-therapeutic and/or cosmetic.

The present invention also discloses a use of a composition of the present invention as disclosed above for hand hygiene.

Now the invention will be demonstrated by the following non-limiting example.

EXAMPLES

Human volunteers study for testing hand sanitizer for long lasting antimicrobial benefits:

For the testing purpose the following compositions as per Example A to C and 1 were prepared.

Example A

Base hand sanitizer composition: The base hand sanitizer composition was prepared as per the following Table 1:

TABLE 1

| Ingredients | Wt % |
|---|---|
| Ethyl Alcohol | 62.000 |
| Isopropyl Alcohol | 3.000 |
| Glycerin | 1.000 |
| Perfume | 0.075 |
| Aminomethyl Propanol | 0.147 |
| Tocopheryl Acetate | 0.050 |
| Tetrasodium EDTA | 0.005 |
| Water | To 100 |

Example B

With the base composition of Example A, 5% of Niacinamide was added. This amount was adjusted with the water amount in the composition.

Example C

With the base composition of Example A, 0.25 wt % of DDAC and 0.1% of BEC was added. This amount was adjusted with the water amount in the composition.

Example 1

With the base composition of Example A, 0.25 wt % of DDAC, 0.1% of BEC and 5% Niacinamide was added. This amount was adjusted with the water amount in the composition.

Testing Protocol:

Step 1:

Marketed Lux® soap bar (Non-antimicrobial) was given to each volunteer to use for bathing, washing hands, washing forearms etc. The volunteers were instructed to use only Lux® soap bar and refrain from using any leave on products (sun screen, hand sanitizer, skin moisturizers, lotion, cream, oil, antimicrobial products etc.) for 7 days. On day 8, each volunteer's hands (palm) were washed with Lux® soap by using hand washing protocol given as described below.

For the washing protocol sterile distilled water was used. The temperature of the water was about 25° C. The soap was dipped in the water for about 10 seconds. After that each palms were wetted with about 100 mL of water. Then the wetted soap was applied on the palms for 5 times back and forth across the length of the palm. After that about 5 mL of water was added on the palms and lathered for about 15 seconds. Then the palms were washed with water to remove the soap completely. The excess water was removed by patting dry using sterile tissue paper.

Step 2:

4 groups were made for the testing purpose with 5 volunteers in each group. The compositions as prepared above (Example A, B, C and 1) were applied to the group in the following manner:

Group-1: Composition of Example A
Group-2: Composition of Example B
Group-3: Composition of Example C
Group-4: Composition of Example 1

After about 20 minutes of washing hands the test compositions were applied as per above Table 2. The protocol for application of test composition is as follows:

300 mg of the respective compositions in respective groups were applied on right hand palm and then it was instructed to the volunteers to spread the compositions all over the surface of palm by using/rubbing both hands until it dries. Again for the second time, 300 mg of the respective compositions in respective groups were applied on the left hand palm then it was instructed to the volunteers to spread the compositions all over the surface of palm by using/rubbing both hands until it dries.

Step 3:

At step 3 the volunteers were instructed to wait for about 3 hours. The temperature of the room where the volunteers were waiting was about 25° C. and the relative humidity was about 45%. During the entire waiting period the volunteers were informed (a) not to touch the palm with forearm/surface/dress/etc., (b) not to wash or splash water on palm and (c) not go outside the study premises (e.g. home, work, shopping etc.).

Step 4:

After about 3 hours of application of the composition (as described in step 2), 0.1 mL of aliquot of the test bacterial suspension was added on each palm (added drop by drop all over the palm including fingers). For this purpose a bacterial culture (about 24 hours old plate culture) of E. coli ATCC 10536 corresponding to $5 \times 10^8$ to $5 \times 10^9$ cells/mL in 10 mM sterile Sodium phosphate buffer was prepared. After adding the culture it was instructed to the volunteers to spread the culture all over the surface of the Palm and fingers for about 30 seconds by rubbing both the palms. It was made sure that the hands were dried at the end of this step.

Step 5:

After about 5 minutes of application of the culture as described in step 4, the hands were placed inside a glove (supplied by 3M India with dimension 7×12 inch) containing 30 mL of sampling buffer and secured the gloves above the wrist with Velcro bands. The sampling buffer was prepared by dissolving 0.4 g of $NA_2HPO_4$, 1.0 g Triton× 100, 100 g of Tween 80 and 11.7 g of Lecithin in 1 L of distilled water followed by adjusting the pH to 7.8±0.1. For this purpose, the materials were procured from Sigma®.

The volunteers were then asked to place their hands on the paddles of the hand scrubbing machine (as per ASTM E2870-13) to recover residual bacteria (as applied in step 4) from palms. The duration of the scrubbing was 2 minutes. The recovered residual bacteria were collected in a sterile containers for analysis.

Step 6:

The containers with residual bacteria as collected in Step 5 was analyzed further to determine the amount residual bacteria (Log cfu/palm) using the standard microbiological technique e.g. spread plating on MacConkey agar plates. Then the plates were incubated for about 24 hours at 37° C.

After 24 hours the colonies were counted using standard plate counting procedure.

The results are summarized below in Table 2

TABLE 2

| Example No | Residual Log cfu/palm | Standard Error |
|---|---|---|
| A | 5.84 | 0.13 |
| B | 5.16 | 0.17 |
| C | 5.52 | 0.24 |
| 1 | 4.58 | 0.22 |

The p value for all the data were calculated to be less than 0.05. This means the data are statistically significant.

From the above table it is evident that the human volunteer study shows that, a composition according to the present invention (Example 1) is significantly better than those examples A to C (controls) in providing antimicrobial benefit. It is also evident that the composition of the present invention provides long lasting benefit (the data were collected after 3 hours).

The invention claimed is:

1. A topical composition comprising:
a) 0.1 to 10% by weight of Niacinamide or its derivatives;
b) 0.01% to 5% by weight of a first quaternary ammonium salt comprising Didecyl Dimethyl Ammonium Chloride;
c) 0.01 to 5% by weight of a second quaternary ammonium salt, wherein the second quaternary ammonium salt is selected from Benzethonium Chloride, Benzalkonium chloride, Polydiallyldimethylammonium chloride or mixtures thereof; and
d) a cosmetically acceptable base;
wherein the composition provides an antimicrobial benefit lasting at least 3 hours.

2. The composition as claimed in claim 1, wherein the amount of Benzethonium Chloride, Benzalkonium chloride and Polydiallyldimethylammonium chloride is in the range of 0.01 to 0.1% by weight.

3. The composition as claimed in claim 1, wherein the amount of Niacinamide or its derivatives is in the range of 2 to 5% by weight.

4. The composition as claimed in claim 1, wherein the composition is in the form of a leave-on composition.

5. The composition as claimed in claim 4, wherein the composition is a hand sanitizer composition.

6. The composition as claimed in claim 5, wherein the composition further comprises an alcohol.

7. The composition as claimed in claim 1, wherein the composition is in the form of a wash-off composition.

8. The composition as claimed in claim 7, further comprising at least one surfactant.

9. The composition of claim 1, wherein the cosmetically acceptable base is selected from a cream, lotion, gel, or emulsion.

10. The composition of claim 1, wherein the cosmetically acceptable base comprises alcohol and water.

11. The composition of claim 10, wherein the alcohol is selected from the group consisting of ethyl alcohol, isopropyl alcohol, and mixtures thereof.

* * * * *